United States Patent
Kast et al.

(10) Patent No.: US 9,943,695 B2
(45) Date of Patent: Apr. 17, 2018

(54) LEAD CONNECTOR WITH GLASS INSULATORS

(75) Inventors: John E. Kast, Hugo, MN (US); Darren A. Janzig, Center City, MN (US); Chris J. Paidosh, St. Anthony, MN (US); Andrew J. Thom, Maple Grove, MN (US); Brad C. Tischendorf, Minneapolis, MN (US); Gerald G. Lindner, Lino Lakes, MN (US)

(73) Assignee: MEDTRONIC, INC, Minneapolis, MN (US)

( * ) Notice: Subject to any disclaimer, the term of this patent is extended or adjusted under 35 U.S.C. 154(b) by 543 days.

(21) Appl. No.: 13/012,957

(22) Filed: Jan. 25, 2011

(65) Prior Publication Data

US 2011/0184479 A1    Jul. 28, 2011
US 2012/0116470 A9    May 10, 2012

Related U.S. Application Data

(60) Provisional application No. 61/299,156, filed on Jan. 28, 2010.

(51) Int. Cl.
*A61N 1/375*    (2006.01)
*H01R 13/187*    (2006.01)
*H01R 24/58*    (2011.01)
*H01R 107/00*    (2006.01)

(52) U.S. Cl.
CPC ......... *A61N 1/3752* (2013.01); *H01R 13/187* (2013.01); *H01R 24/58* (2013.01); *H01R 2107/00* (2013.01)

(58) Field of Classification Search
CPC ..... A61N 1/3752; H01R 24/58; H01R 13/187
USPC .................................................. 607/37, 116
See application file for complete search history.

(56) References Cited

U.S. PATENT DOCUMENTS

| | | |
|---|---|---|
| 5,104,755 A | 4/1992 | Taylor et al. |
| 5,175,067 A | 12/1992 | Taylor et al. |
| 5,821,011 A | 10/1998 | Taylor et al. |
| 6,090,503 A | 7/2000 | Taylor et al. |
| 6,855,456 B2 | 2/2005 | Taylor et al. |
| 7,720,538 B2 | 5/2010 | Janzig et al. |
| 2001/0055716 A1* | 12/2001 | Frysz et al. ............... 429/184 |
| 2008/0208277 A1* | 8/2008 | Janzig et al. ............... 607/37 |
| 2008/0208279 A1* | 8/2008 | Janzig et al. ............... 607/37 |

* cited by examiner

*Primary Examiner* — Carl H Layno
*Assistant Examiner* — Jon Eric C Morales
(74) *Attorney, Agent, or Firm* — Mueting, Raasch & Gebhardt, P.A.

(57) ABSTRACT

A medical device lead connector includes two or more electrically conducting contact rings spaced apart by electrically insulating glass material. The electrically insulating glass material fixes the two or more electrically conducting contact rings in axial alignment.

20 Claims, 7 Drawing Sheets

LEAD CONNECTOR WITH GLASS INSULATORS

RELATED APPLICATION

This patent application claims priority to U.S. Provisional Patent Application Ser. No. 61/299,156, filed Jan. 28, 20101.

BACKGROUND

Implantable active medical devices, such as cardiac rhythm management devices (pacemakers and defibrillators) and a variety of implantable muscle/nerve stimulators, for example, generally include a battery and battery-powered electronic pulse generator contained within a hermetically sealed housing or case and attached to a lead connector housing or block. The lead connector block is often affixed to the hermetically sealed housing with brackets, and/or a medical grade adhesive.

The electronics within the hermetically sealed housing are conductively coupled to the lead connector block with an electrical feedthrough assembly. Electrical feedthroughs serve the purpose of providing a conductive path extending between the interior of a hermetically sealed container and a point outside the hermetically sealed housing. The conductive path through the feedthrough usually includes a conductor pin or terminal that is electrically insulated from the hermetically sealed housing. Many such feedthroughs are known in the art that provide the conductive path and seal the electrical container from its ambient environment. Such feedthroughs typically include a ferrule, and an insulative material such as a hermetic glass or ceramic seal that positions and insulates the pin within the ferrule. Sometimes it is desired that the electrical device include a capacitor within the ferrule and around the terminal, thus shunting any electromagnetic interference (EMI) at high frequencies at the entrance to the electrical device to which the feedthrough device is attached. Typically, the capacitor electrically contacts the pin lead and the ferrule. While this arrangement has proven to be highly reliable, it involves a variety of expensive manufacturing processes and parts that necessarily increase the cost of the resulting product and increases the number of interconnects.

BRIEF SUMMARY

The present disclosure relates to lead connectors with glass insulators. In particular the present disclosure relates to hermetic lead connectors that have contact portions separated by electrically insulating glass material. The electrically insulating glass material can form a hermetic bond with the electrically conducting contact portions of the hermetic lead connectors.

In one illustrative embodiment, a medical device lead connector includes two or more electrically conducting contact rings spaced apart by an electrically insulating glass material. The electrically insulating glass material fixes the two or more electrically conducting contact rings in axial alignment.

In another illustrative embodiment, an implantable active medical device includes a hermetically sealed housing defining a sealed housing interior, a power source, and electronics in electrical communication and disposed within the sealed housing interior, and a lead connector projecting or extending into the sealed housing interior. The lead connector includes a closed end, an open end, an outer surface at least partially defining the sealed housing interior, and an inner surface defining a lead aperture. The lead connector includes two or more electrically conducting contact rings spaced apart by electrically insulating glass material. The two or more electrically conducting contact rings are in electrical communication with the electronics, and the electrically insulating glass material provides a hermetic seal between the lead connector outer surface and the lead connector inner surface.

A further illustrative embodiment, implantable active medical device includes a hermetically sealed housing defining a sealed housing interior, a power source and electronics in electrical communication and disposed within the sealed housing interior, and a lead connector disposed outside of the sealed housing interior. The lead connector is electrically connected to the electronics via a feedthrough into the sealed housing interior. The lead connector includes two or more electrically conducting contact rings spaced apart by electrically insulating glass material. The two or more electrically conducting contact rings are in electrical communication with the electronics via the feedthrough, and the electrically insulating glass material fixing the two or more electrically conducting contact rings in axial alignment.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
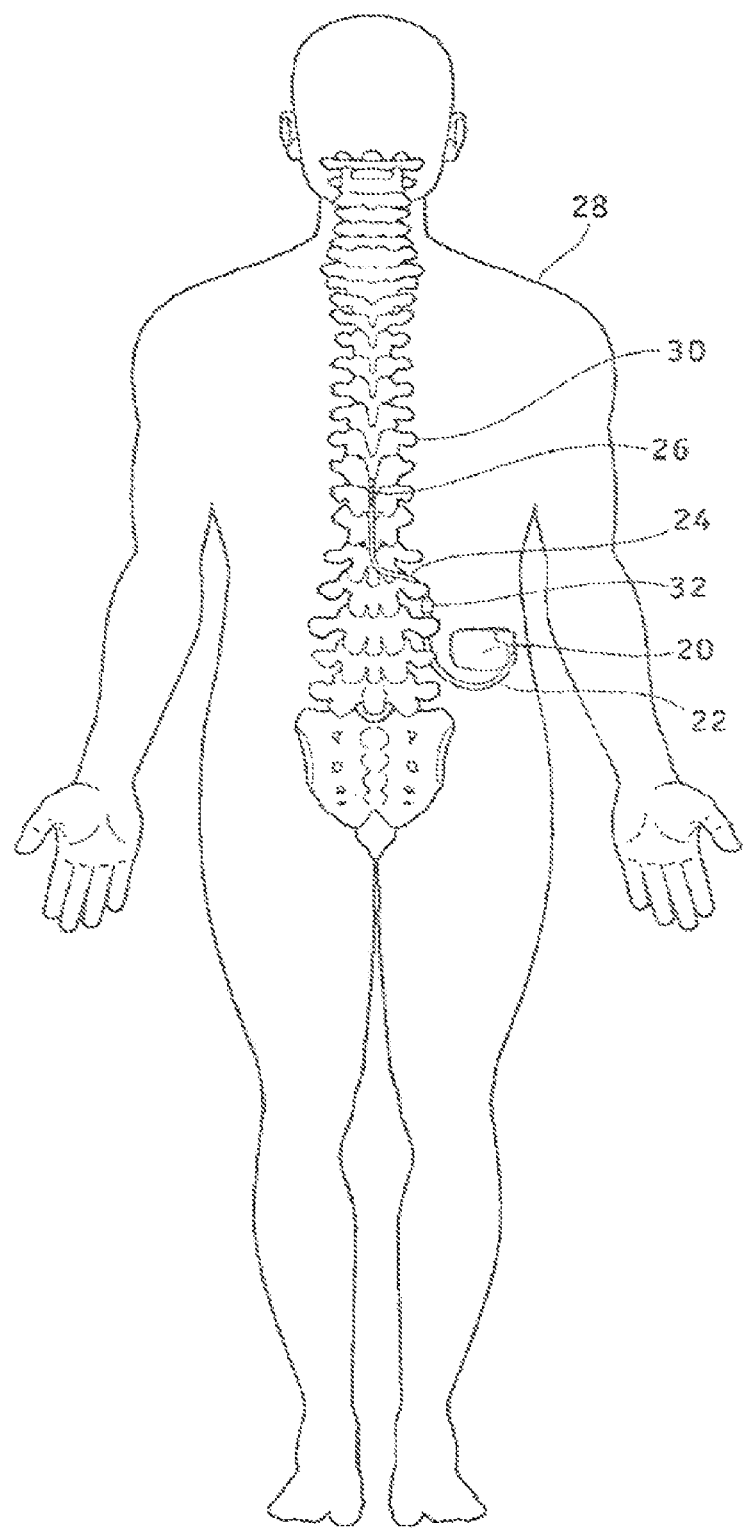
FIG. 1 is a schematic diagram of a an active medical device implanted within a human body.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if a cell depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to lead connectors with glass insulators. In particular the present disclosure relates to hermetic lead connectors that have contact portions separated by electrically insulating glass material. The electrically insulating glass material can form a hermetic bond with the electrically conducting contact portions of the hermetic lead connectors. The electrically insulating glass material eliminates gold or metal brazing material from the hermetic lead connector and thus the manufacturing temperatures of the hermetic lead connector is reduced, in many embodiments, to less than 875 degrees centigrade or a temperature at or about the glass transition temperature of the electrically insulating glass material. In addition, the electrically insulating glass material allows the electrical contact portions of the hermetic lead connector to be closer than has been conventionally available. For example, the pitch between electrical contact portions can be reduced to 0.085 inch or less. Utilizing electrically insulating glass material can provide a number of advantages such as reducing the device manufacturing temperature and reducing the size of the hermetic lead connectors, for example, but not all advantages are necessarily present in all contemplated embodiments. The disclosed lead connectors also can posses pitch control, that is, precise distance control between contact elements within the lead connector since the lead connector is a rigid element. While the present disclosure is not so limited, an appreciation of various aspects of the disclosure will be gained through a discussion of the examples provided below.

FIG. 1 is a schematic diagram of an active medical device 20 implanted within a human body or patient 28. The implanted active medical device 20 is illustrated as a neurostimulator, however, the implanted active medical device 20 can be any "active implantable medical device" or "implantable signal generator" as described above and can be placed in any location within a body cavity or tissue within the body, or on the surface of a patient's skin, as desired.

The active medical device 20 is coupled to a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any suitable useful region of the body such as in the abdomen of a patient 28, and the lead 24 is shown placed somewhere along the spinal cord 30. In many embodiments, the active medical device 20 has one or two leads each having four to eight electrodes. Such a system may also include a physician programmer and a patient programmer (not shown). The active medical device 20 can be considered to be an implantable signal generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patient to provide the desired treatment therapy. While the active medical device 20, in many embodiments, provides electrical stimulation by way of signals, other forms of stimulation may be used as continuous electrical stimulation.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces-Quad® lead available from Medtronic, Inc.), and some are designed to be surgically implanted (e.g. Model 3998 Specify® lead, also available from Medtronic, Inc.). In some embodiments, the lead 24 may contain a paddle at its distal end for housing electrodes 26. In many embodiments, electrodes 26 may include one or more ring contacts at the distal end of lead 24.

Figure 2:
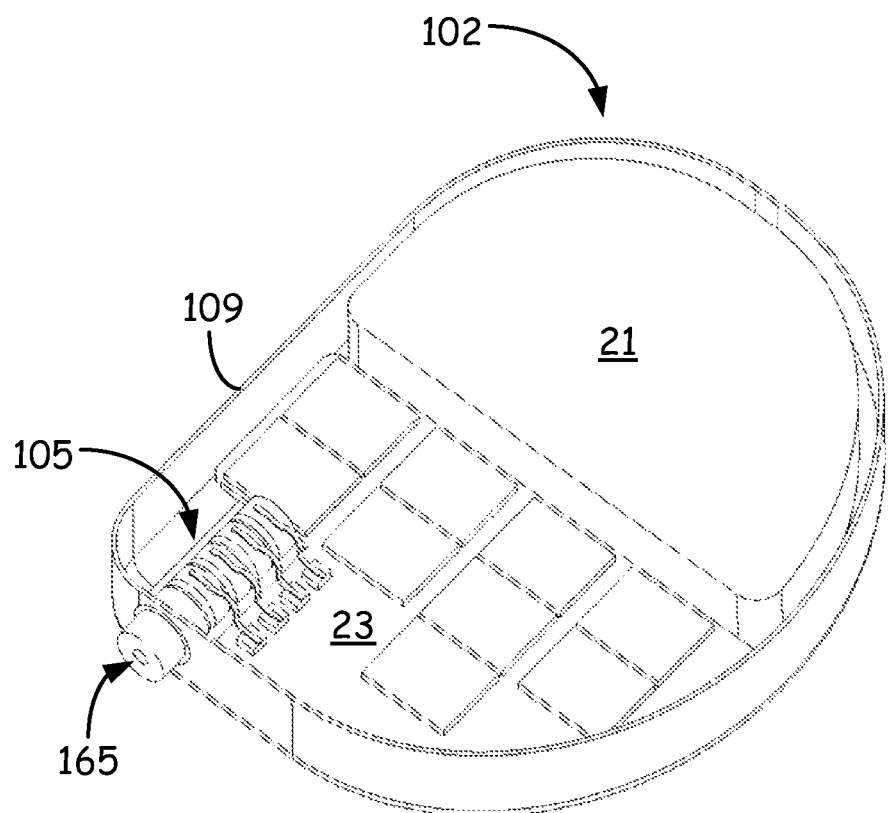
FIG. 2 is a schematic perspective view of an implantable active medical device with an internal hermetic lead connector.
Figure 3:
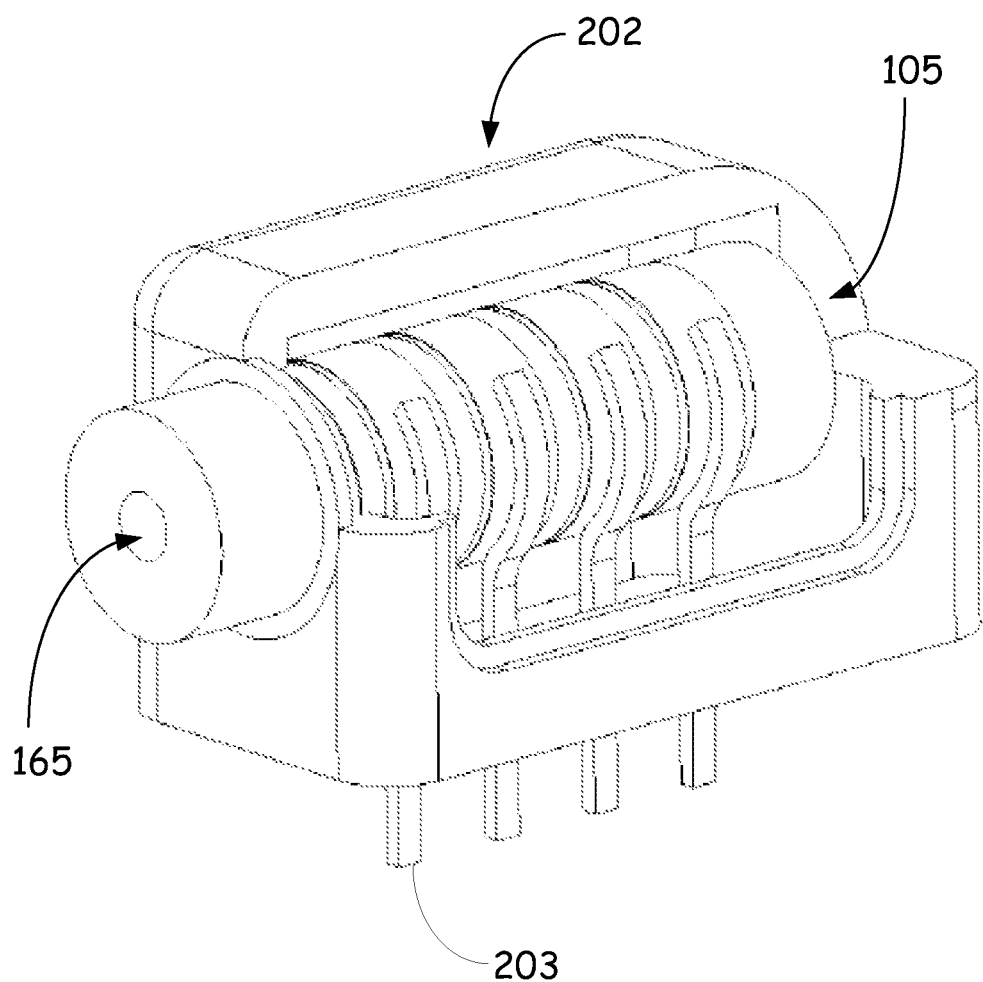
FIG. 3 is a schematic perspective view of another implantable active medical device with an external lead connector.

FIG. 2 is a schematic perspective view of an implantable active medical device 102. FIG. 3 is a schematic cut-away perspective view of an implantable active medical device header 202 with an external hermetic lead connector. Thus the disclosed lead connector 105 can be utilized in a conventional device that utilizes a feedthrough 203 to provide the hermetic barrier (see FIG. 3) or the disclosed lead connector 105 can be utilized to provide the hermetic barrier extending into a device (see FIG. 2). FIG. 3 does not show the hermetic enclosure for the electronics and power source, but it is understood that the hermetic enclosure would be adjacent to the feedthrough 203. FIG. 3 does not rely on the disclosed lead connector 105 to provide the device hermetic barrier, however the disclosed lead connector 105 provides a rigid lead connector with electrical contacts at a fixed pitch.

Figure 4:
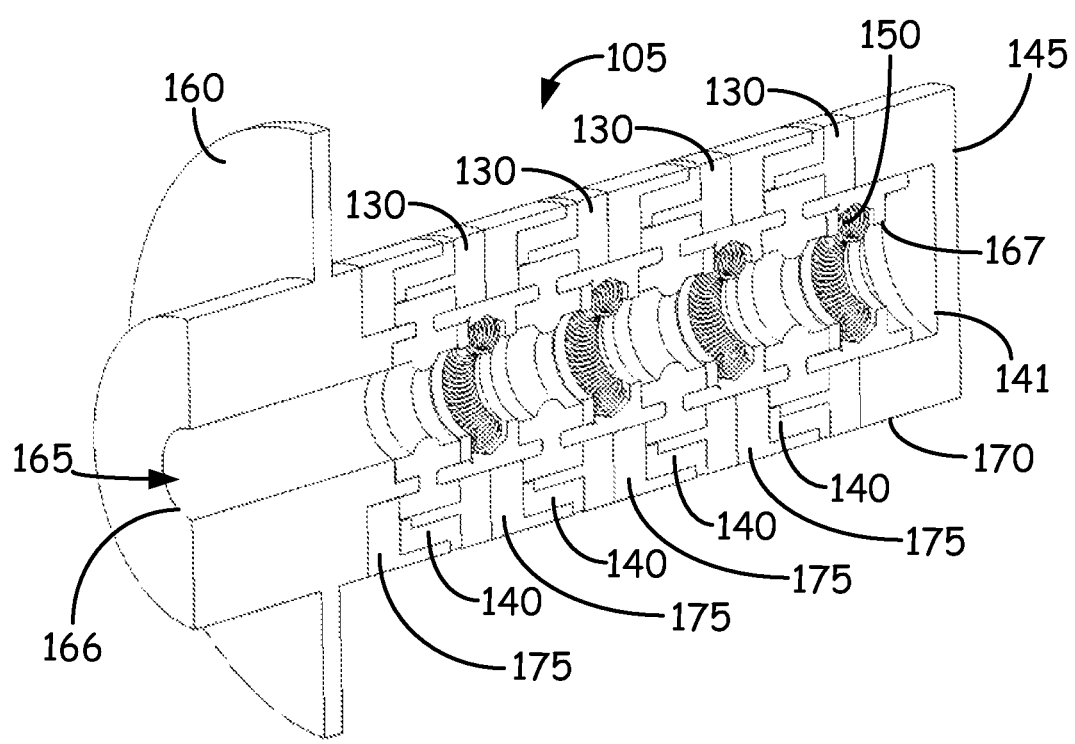
FIG. 4 is a perspective cross-sectional view of an illustrative lead connector.
Figure 5:
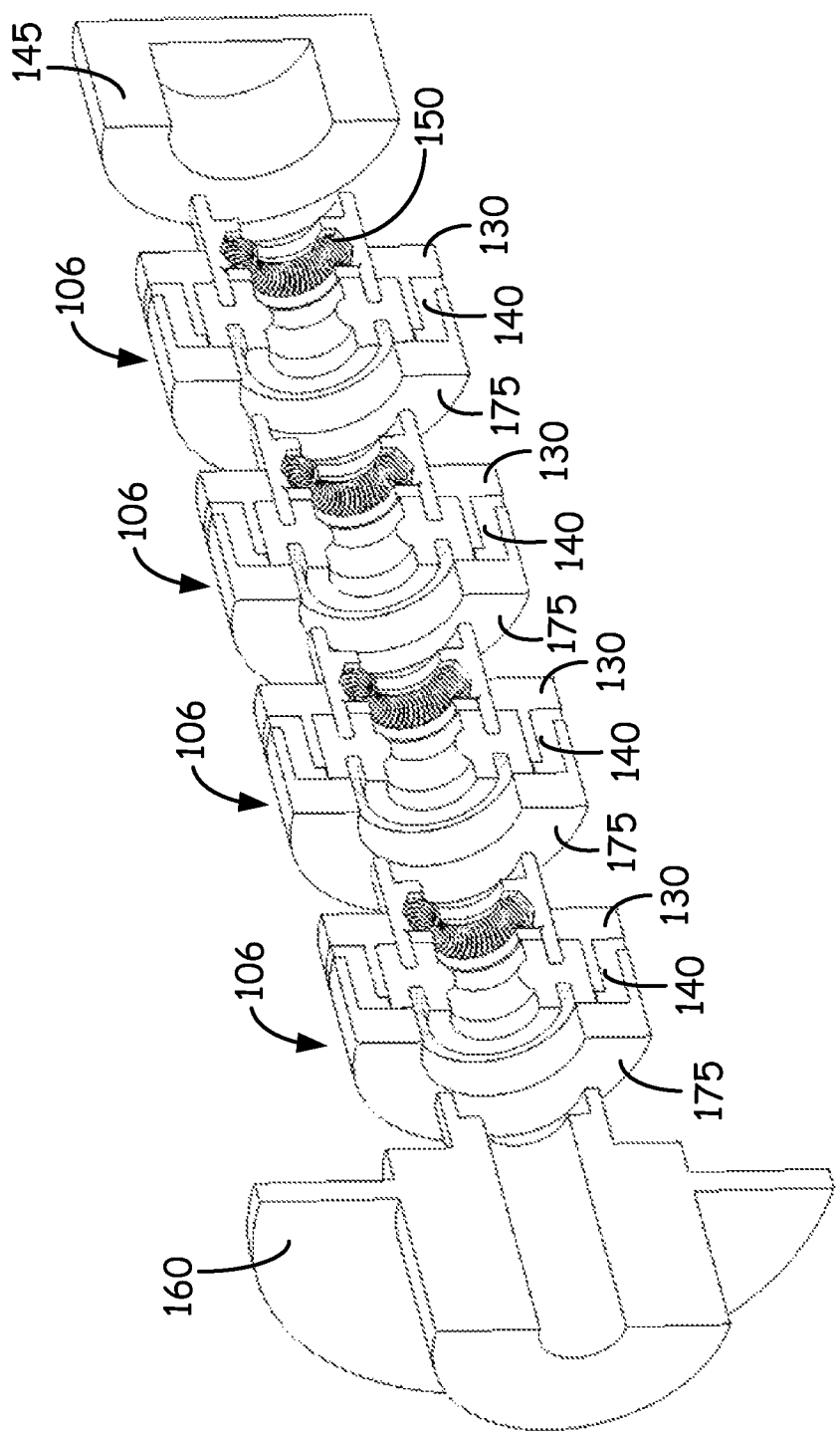
FIG. 5 is an exploded perspective view of the illustrative lead connector shown in FIG. 4.
Figure 6:
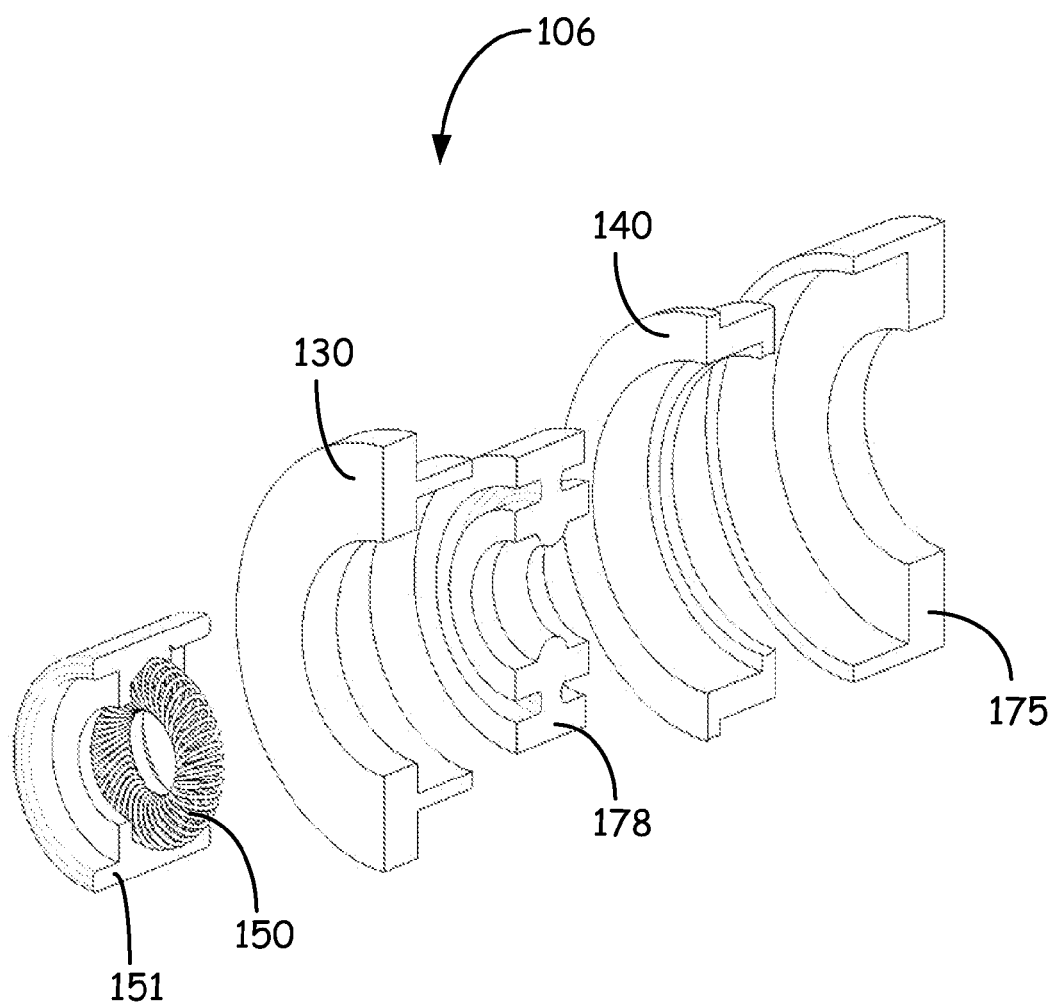
FIG. 6 is an exploded perspective view of one of the illustrative lead connector subassemblies shown in FIG. 5.
Figure 7:
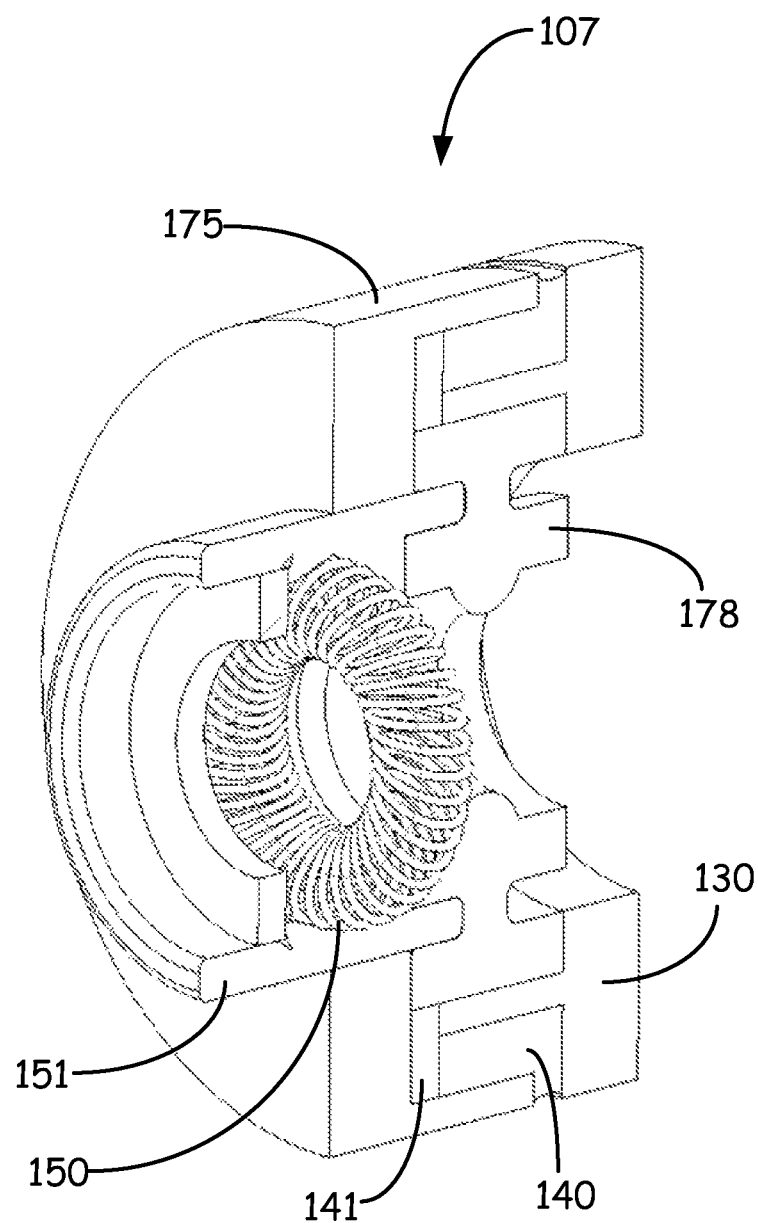
FIG. 7 is a perspective view of another illustrative lead connector sub-assembly.

FIG. 4 is a perspective cross-sectional view of an illustrative lead connector 105. FIG. 5 is an exploded perspective view of the illustrative lead connector 105 shown in FIG. 4. FIG. 6 is an exploded perspective view of one of the illustrative lead connector subassemblies 106 shown in FIG. 5. FIG. 7 is a perspective view of another illustrative lead connector sub-assembly 107 that further includes a ceramic spacer separating electrically conducting portions. While the lead illustrative lead connectors 105 have only one open end, it is contemplated that the lead connectors could have a second open end and form an open lumen through the hermetic envelope of the device.

The active medical device 102 includes a hermetically sealed housing 109 defining a sealed housing interior. The active medical device 102 is illustrated without a cover portion that would complete the hermetic sealed housing 109. A power source 21 and electronics 23 are in electrical communication and are disposed within the sealed housing 109 interior. A lead connector 105 projects into and through the sealed housing 109 interior and has an inner surface or lead receptacle defining an open lumen lead aperture 165. In many embodiments an outer surface of the lead connector 105 at least partially defines the sealed housing interior surface.

The lead connector 105 includes one or more electrically conducting contact rings 130 spaced apart by electrically insulating glass material 140. The one or more electrically conducting contact rings 130 are in electrical communication with the electronics 23 and the lead connector 105 provides a hermetic seal between the sealed housing 109 interior and the lead aperture 165. The electronics 23 generally control the active medical device 102. The power source 21 can be any useful battery or power source such as an inductive coil. In some embodiments, the electronics 23 includes memory. The memory can be any magnetic, electronic, or optical media, such as random access memory (RAM), read-only memory (ROM), electronically-erasable programmable ROM, flash memory, or the like.

The one or more electrically conducting contact rings 130 can be formed as a single element (not shown) or can include a second electrically conducting contact ring 175 that can be welded to the electrically conducting contact ring 130 to form the one or more electrically conducting contact rings 130, 175 as illustrated in the sub-assembly manufacture process described herein.

The one or more electrically conducting contact rings 130 can be formed of any suitable electrically conductive material. In many embodiments, the one or more electrically conducting contact rings 130 are formed of a metallic material such as, for example, titanium, stainless steel, MP35N, niobium, tantalum, platinum, and alloys or combinations thereof. In some embodiments, the one or more electrically conducting contact rings 130 are formed of a metallic material such as, for example, titanium.

The electrically insulating glass material 140 can be formed of any suitable electrically insulating glass material. Glass for formation of electrical insulating member 140 includes boro-alumino, boro-alumino silicate and/or boro silicate type glasses. The element(s) and/or compounds used to form electrical insulating member 140 are selected in a manner to reduce tensile stresses with conducting contact rings 130. For example, electrical insulating member 140, employing glass, has a coefficient of thermal expansion (CTE) value about equivalent to or within 15% of the CTE associated with conducting contact rings 130.

The electrical insulating member 140 may be formed from a glass preform. For example, in making a lead connector 105, the glass preform may be melted so that the molten glass engages conducting contact rings 130 and 175 and subsequently cooled to form insulating member 140. The glass preform can have a composition including about 30-40% $B_2O_3$, about 0-20% CaO, about 0-20% MgO, about 0-20% SrO, about 0-5% $La_2O_3$, about 5-10% $SiO_2$, and about 10-20% $Al_2O_3$, where all percentages represent mole percents. In some embodiments, the composition includes up to about 10% of $MnO_2$, and in some cases the $MnO_2$ may be about 15%. In some embodiments, all or some of the amounts of CaO and/or MgO are replaced with a corresponding amount of SrO, where the amount of SrO does not exceed about 40%. For example, about 10% of CaO and about 5% MgO may be replaced with about 15% SrO. However, the amounts of CaO and MgO are not entirely replaced by SrO, and none of CaO, MgO, and SrO is above 30%. In some embodiments, the composition includes about 30% $B_2O_3$, about 20% CaO, about 20% MgO, about 5% $La_2O_3$, about 10% $SiO_2$, and about 15% $Al_2O_3$.

Various components of the glass composition provide benefits in making a hermetic lead connector 105 and provide the resulting hermetic lead connector 105 with advantageous properties. In particular, $La_2O_3$ provides for better glass flow in melting and forming the electrical insulating member 140, as lower temperatures may be employed compared to glass without $La_2O_3$ or with less $La_2O_3$. Lanthanum oxide also increases the coefficient of thermal expansion (CTE) value of the glass. For example, glass with little or no lanthanum oxide may have a CTE of about 6.5, where glass with lanthanum oxide as described herein may have a CTE of about 8.0. The increased CTE values are closer to the CTE values for metals, such as niobium (Nb), titanium (Ti), platinum (Pt), iridium (Ir) and/or alloys thereof. Similar CTE values reduce the resulting compressive force applied to the glass insulating member when disposed within a subassembly 106. Excessive force may cause tensile cracks in the glass insulating member 140. The propensity for such tensile cracks may be reduced by employing the present compositions.

Strontium oxide within the composition also lowers the processing temperature. For example, as described above, some of the amounts of CaO and/or MgO may be replaced with a corresponding amount of SrO. In this way, the processing temperature of the glass composition may be adjusted, for example, in order to offset temperatures necessary to process amounts of silicon dioxide.

The present composition also limits the amount of $SiO_2$ to about 10%, as this amount provides long-term durability but does not substantially increase the processing temperature. For example, $SiO_2$ in the range of 20% or more increases the temperature required for processing the glass to the point where titanium, which can be used, for example, in conducting contact rings 130 and 175, undergoes a phase transition. This may contribute to titanium parts, or other metal parts approaching the respective metal or alloy melting temperature, to subsequently warp or become distorted. Thus, the present glass composition keeps the amount of silicon dioxide amount low to allow lower processing temperatures where integrity of titanium portion(s) of the hermetic lead connector 105 are maintained.

In some embodiments, the electrically insulating glass material 140 is formed of glass material including: 30 mol % $B_2O_3$; 30 to 40 mol % CaO, MgO, SrO, or combinations thereof; 5 mol % $La_2O_3$; 10 mol % $SiO_2$; and 15 mol % $Al_2O_3$. In many embodiments, the glass insulating material has a glass transition temperature of less than 875 degrees centigrade or has a glass transition temperature in a range from 550 to 700 degrees centigrade.

Other useful glass compositions are described in U.S. Pat. Nos. 5,821,011, 6,090,503, 6,855,456, 5,104,755, and 5,175,067, the disclosure of each of which is incorporated by reference herein. One useful class of glass compositions include BiZnB (bismuth, zinc, boron) glass compositions that can have a glass transition temperature of less then 700 degrees centigrade, or less then 500 degrees centigrade, or less then 350 degrees centigrade. One commercially available BiZnB glass compositions is available under the trade designation DM2995PF from DieMat, Inc. (Byfield, Mass.).

In some embodiments, a filtering capacitor is disposed between the electrically conducting contact rings 130, 175 and the electronics 23. The filtering capacitor can effectively filter out undesirable electromagnetic interference (EMI) from the active medical device 102.

The implantable active medical device described herein eliminates the need for a conventional separate feedthrough block that electrically connects a conventional lead connector block with the hermetically sealed electronics of the implantable active medical device. By placing the lead connector within the hermetically sealed active medical device housing, a direct electrical connection between the lead connector and the electronics can be made (as illustrated in FIG. 2). In addition, the elimination of a feedthrough can reduce the size and volume of the implantable active medical device and can also reduce the number of parts and connections needed to assemble the implantable active medical device.

The illustrated lead connector 105 is an elongate member extending between a lead aperture 165, first open end 166, and end cap 145, and having an inner surface 167 defining an open lumen lead aperture 165. The open lumen lead aperture 165 or lead receptacle 165 is configured to accept one a leads or lead extension, as described above, and electrically couple one or more lead contacts with one or more connector contacts 130, 175 that form the elongate body of the lead connector 105, that in many embodiments is generally cylindrical.

In many embodiments, the lead aperture 165 is a cylindrical open lumen of generally circular cross-sectional area formed by an inner surface of the electrically conducting rings 130, 175 and electrically insulating glass rings 140 bonded together in axial alignment. The lead connector 105 defines a lead connector outer surface 170 and at least a portion of the lead connector outer surface 170 is disposed within the sealed housing 109 interior. In many embodiments, at least a majority of the lead connector outer surface 170 is disposed within the sealed housing 109 interior. In many embodiments, substantially the entire lead connector outer surface 170 is disposed within the sealed housing 109 interior and at least partially defines the sealed housing 109 interior. In some embodiments, the entire lead connector outer surface 170 is disposed within the sealed housing 109 interior.

In the illustrated embodiment, the lead connector 105 is formed of one or more electrically conducting contact rings 130, 175 spaced apart by electrically insulating glass rings 140. The one or more electrically conducting contact rings 130 are in electrical communication with the electronics (described above), and the lead connector 105 body provides a hermetic seal between the sealed housing interior/lead connector outer surface 170 and the lead aperture 165. The one or more electrically conducting contact rings 130, 175 and electrically insulating glass rings 140 are assembled in axial alignment to form the lead connector 105.

The one or more electrically conducting contact rings 130, 175 can include one or more additional contact elements in electrical contact with and optionally disposed within each of the one or more electrically conducting contact rings 130, 175. These one or more additional contact elements are configured to provide electrical communication between one or more electrically conducting contact rings 130, 175 and a lead contact received within the lead aperture 165. In many embodiments, these contact elements are electrically conductive and resilient to provide an interference fit between the electrically conducting contact ring 130, 175 and lead contact received within the lead aperture 165.

Examples of contact elements include, but are not limited to, spring elements. In many embodiments, the contact element includes an annular helical coil 150 (i.e., continuous coil spring 150) disposed adjacent an inner surface of the electrically conducting contact ring 130. The helical annular coil 150 can be formed of any suitable electrically conductive material such as, for example, a metal like gold, silver, titanium or the like. When a lead in inserted into the lead aperture 165, the lead and lead contact(s) can deflect the annular helical coil 150 and form an electrical contact between the lead contact and the electrically conducting contact ring 130. The continuous coil spring 150 frictionally provides an electrical and mechanical engagement with a lead contact and the adjacent electrically conducting contact ring 130. The continuous coil spring 150 can be held in place with a spring holder 151, as illustrated in FIG. 6 and FIG. 7.

A mounting flange 160 can be fixed to the lead connector 105 adjacent the open end 166. The mounting flange 160 can be brazed or welded, for example, to the hermetically sealed housing 109. In some embodiments, the mounting flange 160 is brazed or welded to an exterior surface of the hermetically sealed housing 109. In other embodiments, the mounting flanges 160 are brazed or welded to an interior surface of the hermetically sealed housing 109. A retention member (not shown) such as for example, a set screw, can be disposed on the lead connector 105 adjacent to the open end 166 and can assist in mechanical retention of the lead disposed within the lead aperture 165.

The lead connector 105 can be formed by any suitable method. In many embodiments, the lead connector 105 is formed by assembling two or more lead connector subassemblies 106. FIG. 6 is an exploded perspective cut-away view of the illustrative subassembly 106 shown in FIG. 5. FIG. 7 is a perspective cut-away view of another illustrative subassembly 107 that includes a ceramic spacer ring 141 separating the electrically conducting contact rings 130 and 175. Each lead connector subassembly 106 or 107 can be arranged in axial alignment and bonded utilizing a metal-to-metal bonding technique such as, for example, laser welding, to form the lead connector 105. In some embodiments, the subassembly 107 includes a wiper seal 178 that can assist in electrical isolation of adjacent electrical contacts and also to mitigate fluid transmission within the lead aperture.

In the exemplary embodiment shown, each lead connector subassembly 106 includes an electrically insulating glass ring 140 fixed between the electrically conducting contact ring 130 and an attachment ring or electrically conducting spacer ring 175. Thus, the electrically conducting spacer ring 175 is affixed to a first side of the electrically insulating glass ring 140 and the electrically conducting contact ring 130 is affixed to a second opposing side of the electrically insulating glass ring 140. The lead connector subassembly 106 includes the electrically insulating glass ring 140 bonding the electrically conducting contact ring 130 to the electrically conducting spacer ring 175. The electrically insulating glass ring 140 assists in creating the hermetic seal between the between the sealed housing interior/lead connector outer surface 170 and the lead aperture 165.

The electrically conducting spacer ring 175 can be formed of any useful electrically conductive material. In many embodiments, the electrically conducting spacer ring 175 is formed of a metallic material such as, for example, titanium, stainless steel, MP35N, niobium, tantalum, platinum, and alloys or combinations thereof. In some embodiments, the one electrically conducting spacer ring 175 is formed of a metallic material such as, for example, titanium.

As illustrated in FIG. 5 and FIG. 7, the electrically conducting contact ring 130 and electrically conducting spacer ring 175 form an overlapping joint. The electrically insulating glass material 140 at least partially filling the overlapping joint space separating the electrically conducting contact ring 130 and electrically conducting spacer ring 175. The overlapping joint improves the structural integrity of the electrically insulating glass material 140 bond.

Thus, embodiments of the LEAD CONNECTOR WITH GLASS INSULATORS are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A medical device lead connector comprising:
two or more electrically conducting contact rings spaced apart by electrically insulating glass material, the electrically insulating glass material directly fixing the two or more electrically conducting contact rings in axial alignment, without forming a weld and without a braze between the electrically insulating glass material and the electrically conducting contact rings, wherein the electrically insulating glass material comprises a coefficient of thermal expansion (CTE) value about equivalent to or within 15% of the CTE associated with the two or more electrically conducting contact rings and has a glass transition temperature of less than 875 degrees centigrade.

2. A medical device lead connector according to claim 1, wherein the lead connector comprises a plurality of ring subassemblies fixed in axial alignment and each ring subassembly comprises the glass insulating material fixed, in a lateral direction, between an inner portion of an electrically conducting contact ring and an outer portion of an electrically conducting spacer ring.

3. A medical device lead connector according to claim 2, wherein adjacent ring subassemblies are welded together to form a rigid medical device lead connector.

4. A medical device lead connector according to claim 1, wherein the glass insulating material comprises:
30 mol % $B_2O_3$;
30 to 40 mol % CaO, MgO, SrO, or combinations thereof;
5 mol % $La_2O_3$;
10 mol % SiO2; and
15 mol % $Al_2O_3$.

5. A medical device lead connector according to claim 1, wherein the two or more electrically conducting contact rings are spaced apart by a ceramic ring and the electrically insulating glass material.

6. A medical device lead connector according to claim 2, wherein each ring subassembly comprises a ceramic ring disposed between the electrically conducting contact ring and the electrically conducting spacer ring.

7. A medical device lead connector according to claim 6, wherein the ceramic ring separates the electrically conducting contact ring and the electrically conducting spacer ring.

8. An implantable active medical device comprising:
a hermetically sealed housing defining a sealed housing interior;
a power source and electronics in electrical communication and disposed within the sealed housing interior; and
a lead connector projecting into the sealed housing interior and having a closed end, an open end, an outer surface at least partially defining the sealed housing interior, and an inner surface defining a lead aperture, the lead connector comprising two or more electrically conducting contact rings spaced apart by electrically insulating glass material, the electrically insulating glass material separating the directly fixing the two or more electrically conducting contact rings together in axial alignment, without forming a weld and without a braze between the electrically insulating glass material and the electrically conducting contact rings, the two or more electrically conducting contact rings in electrical communication with the electronics, and the electrically insulating glass material providing a hermetic seal between the lead connector outer surface and the lead connector inner surface, wherein the electrically insulating glass material comprises a coefficient of thermal expansion (CTE) value about equivalent to or within 15% of the CTE associated with the two or more electrically conducting contact rings and has a glass transition temperature of less than 875 degrees centigrade.

9. An implantable active medical device according to claim 8, wherein the lead connector comprises a plurality of ring subassemblies fixed in axial alignment.

10. An implantable active medical device according to claim 9, wherein each ring subassembly comprises the glass insulating material fixed, in a lateral direction, between an inner portion of an electrically conducting contact ring and an outer portion of an electrically conducting spacer ring.

11. An implantable active medical device according to claim 10, wherein the glass insulating material directly bonds the electrically conducting contact ring and the electrically conducting spacer ring.

12. An implantable active medical device according to claim 10, wherein each ring subassembly comprises a ceramic ring disposed between the electrically conducting contact ring and the electrically conducting spacer ring.

13. An implantable active medical device according to claim 8, wherein the glass insulating material comprises:
30 mol % $B_2O_3$;
30 to 40 mol % CaO, MgO, SrO, or combinations thereof;
5 mol % $La_2O_3$;
10 mol % SiO2; and
15 mol % $Al_2O_3$.

14. An implantable active medical device according to claim 8, wherein the glass insulating material has a glass transition temperature of less than 700 degrees centigrade.

15. An implantable active medical device according to claim 8, wherein the lead connector comprises a plurality of ring subassemblies fixed in axial alignment and a first ring subassembly electrically conducting contact ring is welded to an adjacent second ring subassembly electrically conducting spacer ring.

16. An implantable active medical device according to claim 8, wherein the lead connector comprises a plurality of ring subassemblies welded in axial alignment and each ring subassembly has substantially similar dimensions.

17. An implantable active medical device according to claim 8, wherein the lead connector comprises a mounting flange adjacent to the open end and the mounting flange is fixed to the hermetically sealed housing.

18. An implantable active medical device according to claim 8, wherein the two or more electrically conducting contact rings are spaced apart by a ceramic ring and the electrically insulating glass material.

19. An implantable active medical device comprising:
- a hermetically sealed housing defining a sealed housing interior;
- a power source and electronics in electrical communication and disposed within the sealed housing interior; and
- a lead connector disposed outside of the sealed housing interior, the lead connector electrically connected to the electronics via a feedthrough into the sealed housing interior, the lead connector comprising two or more electrically conducting contact rings spaced apart by electrically insulating glass material, the two or more electrically conducting contact rings in electrical communication with the electronics via the feedthrough, and the electrically insulating glass material directly fixing the two or more electrically conducting contact rings in axial alignment, without forming a weld and without a braze between the electrically insulating glass material and the electrically conducting contact rings, wherein the electrically insulating glass material comprises a coefficient of thermal expansion (CTE) value about equivalent to or within 15% of the CTE associated with the two or more electrically conducting contact rings and has a glass transition temperature of less than 875 degrees centigrade.

20. An implantable active medical device according to claim 19, wherein the two or more electrically conducting contact rings are spaced apart by a ceramic ring and the electrically insulating glass material.

* * * * *